United States Patent
Yumioka et al.

(10) Patent No.: US 10,376,452 B2
(45) Date of Patent: Aug. 13, 2019

(54) CLEANSING COMPOSITION

(71) Applicant: AJINOMOTO CO., INC., Tokyo (JP)

(72) Inventors: Rina Yumioka, Kawasaki (JP); Kazuhiko Tobita, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 15/638,984

(22) Filed: Jun. 30, 2017

(65) Prior Publication Data
US 2018/0000709 A1 Jan. 4, 2018

(30) Foreign Application Priority Data

Jul. 1, 2016 (JP) .................. 2016-131878
May 23, 2017 (JP) .................. 2017-101889

(51) Int. Cl.
| | |
|---|---|
| *A61K 8/44* | (2006.01) |
| *A61Q 5/02* | (2006.01) |
| *A61Q 19/10* | (2006.01) |
| *C11D 1/10* | (2006.01) |
| *C11D 1/94* | (2006.01) |
| *C11D 3/43* | (2006.01) |
| *C11D 1/37* | (2006.01) |

(52) U.S. Cl.
CPC .................. *A61K 8/44* (2013.01); *A61Q 5/02* (2013.01); *A61Q 19/10* (2013.01); *C11D 1/10* (2013.01); *C11D 1/37* (2013.01); *C11D 1/94* (2013.01); *C11D 3/43* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

2011/0165106 A1* 7/2011 Molenda ................ A61K 8/442
424/70.9

FOREIGN PATENT DOCUMENTS

| JP | 5-156287 A | | 6/1993 |
|---|---|---|---|
| JP | 06-264091 | * | 9/1994 |
| JP | 11-323379 A | | 11/1999 |
| JP | 2001-31993 A | | 2/2001 |
| JP | 2002-020267 | * | 1/2002 |

* cited by examiner

*Primary Examiner* — Tanisha Diggs
(74) *Attorney, Agent, or Firm* — Oblon, McClelland, Maier & Neustadt, L.L.P.

(57) ABSTRACT

Provided is a cleansing composition of acyl amino acid, showing good foamability and good lather retention effect, which is rinsed off quickly and affords superior skin texture after drying. A cleansing composition containing the following components (A), (B) and (C), wherein a weight ratio of (A)/(B) is 0.2-5 and a weight ratio of ((A)+(B))/(C) is 2.5-10.0:

(A) N-lauroylglycine or a salt thereof
(B) N-myristoylglycine or a salt thereof
(C) N-acyl acidic amino acid having an acyl group having 8-24 carbon atoms, or a salt thereof.

18 Claims, No Drawings

CLEANSING COMPOSITION

TECHNICAL FIELD OF THE INVENTION

The present invention relates to a cleansing composition superior in the lather property and texture after rinsing or washing.

BACKGROUND OF THE INVENTION

In recent years, cleansing agents for body or hair have been desired to show not only high detergency but also low irritancy to the skin and good sense of use. Among these, amino acid type cleansing agent components are attracting attention and, for example, cleansing agents combining an acyl acidic amino acid and an acyl neutral amino acid (patent documents 1, 2), and a cleansing agent combining N-lauroylglycine salt and N-myristoylglycine salt (patent document 3) have been studied. Among acyl acidic amino acids, acyl glutamate is characterized by its mildness and property to impart a moist feeling. However, it is also known that its foamability is not satisfactory and a slimy feeling is imparted resulting in low rinsability, when the amount of acyl glutamate is large.

DOCUMENT LIST

Patent Documents patent document 1: JP-A-5-156287
patent document 2: JP-A-11-323379
patent document 3: JP-A-2001-31993

SUMMARY OF THE INVENTION

Problems to be Solved by the Invention

The present invention aims to provide a cleansing composition showing good foamability and good lather retention effect, which is rinsed off quickly and affords superior skin texture after drying.

Means of Solving the Problems

The present inventors have conducted intensive studies in an attempt to solve the above-mentioned problems, and found that a cleansing composition superior in foamability and lather retention effect, which is rinsed off quickly and affords superior texture after drying such as refreshed feeling, moist feeling and the like, can be obtained by blending N-lauroylglycine or a salt thereof, N-myristoylglycine or a salt thereof, and particular N-acyl acidic amino acid or a salt thereof with other particular components to give a composition having a particular mixing ratio, which resulted in the completion of the present invention.

Therefore, the present invention provides the following.
[1] A cleansing composition comprising the following components (A), (B) and (C), wherein a weight ratio of (A)/(B) is 0.2-5 and a weight ratio of ((A)+(B))/(C) is 2.5-10.0:
(A) N-lauroylglycine or a salt thereof
(B) N-myristoylglycine or a salt thereof
(C) N-acyl acidic amino acid having an acyl group having 8-24 carbon atoms, or a salt thereof.
[2] The cleansing composition of [1], wherein the acidic amino acid of (C) is glutamic acid or aspartic acid.
[3] The cleansing composition of [1] or [2], wherein (C) N-acyl acidic amino acid salt is a salt with at least one selected from the group consisting of sodium, potassium and triethanolamine.
[4] The cleansing composition of any one of [1]-[3], wherein (C) is at least one selected from the group consisting of N-lauroylglutamic acid, N-myristoylglutamic acid, N-cocoylglutamic acid, sodium salts thereof, potassium salts thereof and triethanolamine salts thereof.
[5] The cleansing composition of any one of [1]-[4], wherein (A) N-lauroylglycine salt is a salt with at least one selected from the group consisting of sodium, potassium and triethanolamine.
[6] The cleansing composition of any one of [1]-[5], wherein (B) N-myristoylglycine salt is a salt with at least one selected from the group consisting of sodium, potassium and triethanolamine.
[7] The cleansing composition of any one of [1]-[6], which is a liquid.
[8] The cleansing composition of [7], having pH 6-10.

Effect of the Invention

According to the present invention, a cleansing composition superior in frothing ability such as foamability and lather retention, and usability such as quick rinsing and the like can be provided.

According to the present invention, a cleansing composition capable of providing gentle moist finish of washing with refreshed feeling after washing can be provided.

DESCRIPTION OF EMBODIMENTS

The present invention relates to a cleansing composition comprising (A) N-lauroylglycine or a salt thereof, (B) N-myristoylglycine or a salt thereof and (C) N-acylacidic amino acid having an acyl group having 8-24 carbon atoms, or a salt thereof at a particular ratio (hereinafter sometimes to be abbreviated as the cleansing composition of the present invention).

As a salt of (A) N-lauroylglycine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, alkali metal salt and alkanolamine salt are preferable, and sodium salt, potassium salt and triethanolamine salt are more preferable, for obtaining a cleansing composition superior in foamability and lather retention.

Component (A) may be in the form of a salt, which is obtained by adding, when the cleansing composition of the present invention is prepared, N-lauroylglycine together with a substance (e.g., sodium hydroxide, potassium hydroxide, TEA etc.) that forms the above-mentioned salts, thus performing neutralization.

As a salt of (B) N-myristoylglycine, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, alkali metal salt and alkanolamine salt are preferable, and sodium salt, potassium salt, triethanolamine salt are more preferable for obtaining a cleansing composition superior in foamability and lather retention.

Component (B) may be in the form of a salt, which is obtained by adding, when the cleansing composition of the present invention is prepared, N-myristoylglycine together with a substance (e.g., sodium hydroxide, potassium hydroxide, TEA etc.) that forms the above-mentioned salts, thus performing neutralization.

As component (C) N-acyl acidic amino acid or a salt thereof in the present invention, any of D form, L form and DL form can be used. Each of the N-acyl acidic amino acid or a salt thereof may be used alone, or two or more kinds thereof may be used in a mixture at any ratio.

The acyl group of component (C) N-acyl acidic amino acid or a salt thereof in the present invention is an acyl group induced from fatty acid having 8-24 carbon atoms, and an acyl group induced from fatty acid having 8-22 carbon atoms is preferable, and an acyl group induced from fatty acid having 8-18 carbon atoms is more preferable. Examples of the acyl group include an acyl group induced from lauric acid, myristic acid, palmitic acid, stearic acid, oleic acid, isostearic acid or the like, a mixture thereof such as beef tallow fatty acid, coconut oil fatty acid, palm kernel oil fatty acid and the like can be mentioned, an acyl group induced from lauric acid, myristic acid or coconut oil fatty acid is preferable, and an acyl group induced from lauric acid or coconut oil fatty acid is more preferable.

While the acidic amino acid of component (C) in the present invention is not particularly limited as long as it is an acidic amino acid, examples thereof include glutamic acid, aspartic acid and the like, and glutamic acid and aspartic acid are preferable.

As a salt of N-acyl acidic amino acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Of these, alkali metal salt and alkanolamine salt are preferable, and sodium salt, potassium salt, triethanolamine are more preferable, since one superior in foamability and preservation stability is obtained.

Component (C) may be in the form of a salt, which is obtained by adding, when the cleansing composition of the present invention is prepared, N-acyl acidic amino acid together with a substance (e.g., sodium hydroxide, potassium hydroxide, TEA etc.) that forms the above-mentioned salts, thus performing neutralization. Furthermore, component (C) may contain unneutralized N-acyl acidic amino acid.

Specific examples of the N-acyl acidic amino acid salt to be used in the present invention include monosodium salt, monopotassium salt, triethanolamine salt and the like of N-lauroylglutamic acid, N-myristoylglutamic acid, N-cocoyl (coconut oil fatty acid acyl) glutamic acid, N-lauroylaspartic acid, N-myristoylaspartic acid or N-cocoylaspartic acid. One kind of these may be used or two or more kinds thereof may be used in a mixture. Of these, a sodium salt, a potassium salt or a triethanolamine salt of N-lauroylglutamic acid, N-myristoylglutamic acid or N-cocoylglutamic acid, or a mixture thereof is preferable, and a potassium salt, a sodium salt or a triethanolamine salt of N-lauroylglutamic acid or N-cocoylglutamic acid, or a mixture thereof is more preferable.

The cleansing composition of the present invention is characterized in that a weight ratio of (A)/(B) is 0.2-5. The weight ratio of (A)/(B) is preferably 0.3-3.5, more preferably 0.4-2.3. A cleansing composition superior in the sense of use and the like can be provided when the weight ratio is within these ranges.

The cleansing composition of the present invention is also characterized in that a weight ratio of ((A)+(B))/(C) is 2.5-10.0. The weight ratio of ((A)+(B))/(C) is preferably 3.0-9.5, more preferably 3.5-9.0. A cleansing composition superior in the sense of use, quick rinsing off, lather retention, moist feeling after drying and the like can be provided when the weight ratio is within these ranges.

As (A), (B) and (C) in the present invention, synthesized products and commercially available products can be used.

The form of the cleansing composition of the present invention is not particularly limited, and may be any form, for example, solid, liquid, paste, gel, powder, granule, cream and the like. Of these, liquid, powder or granule is preferable, and liquid is particularly preferable, since it is superior in handling.

When the cleansing composition of the present invention is a liquid cleansing composition, its pH is generally 6-10, preferably 7-10, more preferably 7.5-9.5. A cleansing composition superior in the sense of use can be provided when the pH is within these ranges.

When the cleansing composition of the present invention is other than a liquid, its pH is defined to be pH of a 10% aqueous solution thereof (25° C.), which is in accordance with the above-mentioned pH ranges.

The cleansing composition of the present invention can be produced by a method known per se. For example, a mixture of the above-mentioned respective components and other additives are mixed, and the mixture is generally heated at 80-90° C. for 5 min-10 min to uniformly dissolve each component in a suitable solvent such as water and the like. The obtained composition can be prepared as a cleansing composition in a desired form by a method known per se. For example, each component is uniformly dissolved by heating, which is injected in a mold, solidified by cooling, and dried and matured to give a solid cleansing composition.

When the cleansing composition of the present invention is a liquid, a suitable solvent is added such that the total content of components (A), (B) and (C) is generally 15-40 wt %, preferably 20-35 wt %, more preferably 25-30 wt %, and the liquid can be prepared by a method known per se.

Various generally-used additives can be added to the cleansing composition of the present invention as long as the effect of the invention is not inhibited.

For example, starting materials and the like described in various official compendia such as Japanese Standards of Cosmetic Ingredients, Cosmetic Ingredients Codex, Japanese Standard of Quasi-drug Ingredients, the Japanese Pharmacopoeia, Japanese Standards for Pharmaceutical Ingredient, Japan's Specifications and Standards for Food Additives and the like, such as higher alcohols such as cetyl alcohol, stearyl alcohol, behenyl alcohol, isostearyl alcohol, octyldodecanol, oleyl alcohol, myristyl alcohol and the like; higher fatty acids such as hardened beef tallow fatty acid, coconut oil fatty acid, palm oil fatty acid and the like and a salt thereof (excluding fatty acid having 6-24 carbon atoms or a salt thereof); moisturizers such as trimethylglycine and the like; surfactants such as anionic surfactant (excluding (C) in the present invention), cationic surfactant, amphoteric surfactant, non-ionic surfactant and the like; synthetic fats and oils such as vegetable oil, animal fats and oils, natural fat and oil derivatives, mineral fats and oils, lower and higher fatty acid ester and the like; silicone compound; polymer substance; animal and plant extracts; amino acid; nucleic acid; vitamin; enzyme; anti-inflammatory agent; antimicrobial agent; preservative; antioxidant; ultraviolet absorber; chelating agent; adiaphoretic; oxidation dye; ph adjuster; pearly sheen agent; and the like can be mentioned.

The cleansing composition of the present invention can be used for shampoo, facial cleanser, body shampoo, hand soap, shaving agent, cleansing agent for kitchen and laundry detergent, according to the object of use.

EXAMPLES

While the present invention is explained in more detail in the following by referring to Examples, the present invention is not limited to these Examples. In the present specification, % means wt % unless particularly indicated.
[Preparation of Cleansing Composition]

Respective components in the amounts shown in Tables 1-4 were mixed, and the mixture was heated to 70-80° C. to uniformly dissolve each component. After cooling, potassium hydroxide was added to adjust the pH to 9.0 to give liquid cleansing compositions (in Tables, value of each component is in wt %).

Potassium Lauroyl Glycinate (Synthetic Example 1)

Glycine (45.99 g, 0.61 mol), lauric acid 94.94 (0.47 mol), 85% potassium hydroxide (29.09 g, 0.44 mol), and purified water (35.30 g) were mixed, and the mixture was reacted under a nitrogen stream at 150° C. for 15 hr. After the reaction, 188.59 g from the obtained resultant product was diluted with purified water (274.71 g) to give an aqueous potassium lauroyl glycinate solution.
Potassium Myristoyl Glycinate (Synthetic Example 2)

Glycine (43.09 g, 0.57 mol), myristic acid (101.49 g, 0.45 mol), 85% potassium hydroxide (27.20 g, 0.41 mol), and purified water (33.02 g) were mixed, and the mixture was reacted under a nitrogen stream at 150° C. for 15 hr. After the reaction, 191.33 g from the obtained resultant product was diluted with purified water (290.18 g) to give an aqueous potassium myristoyl glycinate solution.

Potassium Lauroyl Glutamate (Synthetic Example 3)

Monosodium L-glutamate monohydrate (240 g, 1.28 mol) was suspended in purified water (377 mL), 48% potassium hydroxide (130.9 g) was added thereto to give an aqueous solution (pH 11.5), which was cooled to 15° C. Thereto were simultaneously added dropwise lauroyl chloride (259.2 g) and 48% aqueous potassium hydroxide solution (165.9 g). The temperature of the reaction system was raised to 30° C. and the mixture was stirred for 1.5 hr, heated to 70° C., and stirred for 1 hr to complete the reaction. To the obtained reaction product were added purified water and 35% hydrochloric acid to give aqueous potassium lauroyl glutamate solution adjusted to pH 8.9.

Potassium cocoyl glutamate (Synthetic Example 4)

Monosodium L-glutamate monohydrate (120 g, 0.64 mol) was suspended in purified water (188.4 mL), 48% potassium hydroxide (65.5 g) was added thereto to give an aqueous solution (pH 11.5), which was cooled to 15° C. Thereto were simultaneously added dropwise coconut oil fatty acid chloride (129.6 g) and 48% aqueous potassium hydroxide solution (82.9 g). The temperature of the reaction system was raised to 30° C. and the mixture was stirred for 1.5 hr, heated to 70° C., and stirred for 1 hr to complete the reaction. To the obtained reaction product were added purified water and 35% hydrochloric acid to give aqueous potassium cocoyl glutamate solution adjusted to pH 8.9.

Respective cleansing compositions obtained according to the above were evaluated for various properties according to the following criteria. The results are shown in Tables 1-4.
[Foamability, Lather Retention]

Respective compositions were adjusted to 0.24% with ion exchange water, 50 mL thereof was stirred by a domestic mixer (trade name "MILLSER", manufactured by Iwatani Corporation) for 5 sec, and the lather amount (mL) was measured after standing for 1 min and 5 min.

The "lather amount", was evaluated based on the lather amount (mL) 1 min later as the standard.
⊙; not less than 260
○; not less than 240 and less than 260
Δ; not less than 230 and less than 260
x; less than 230

The lather amount (mL) was measured 5 min later and the "lather retention" was evaluated based on the lather amount (mL) 5 min later/lather amount 1 min later×100 as the standard.
⊙; not less than 90
○; not less than 85 and less than 90
Δ; not less than 80 and less than 85
x; less than 80
[Sense of Use]

Ten male and female panelists washed hands using respective compositions and tap water at 40° C., and respective compositions were evaluated for foamability (lather), easiness of rinsing, and texture of hands after drying according to the following criteria.
Foamability: 3; good, 2; usual, 1; weak.
Easiness of rinsing: 3; fast, 2; usual, 1; late.
Texture after drying: 3; with moist feeling and clarifying feeling, 2; usual, 1; no moist feeling and clarifying feeling.

Mean of the aforementioned criteria was calculated, and evaluation was made as follows based on the mean.
good (○); not less than 2.2
usual (Δ); not less than 1.3 and less than 2.2
bad (x); less than 1.3

TABLE 1

| | Example (lauroyl glutamic acid) | | | | | | Example (cocoyl glutamic acid) | | | | | |
|---|---|---|---|---|---|---|---|---|---|---|---|---|
| | 1 | 2 | 3 | 4 | 5 | 6 | 7 | 8 | 9 | 10 | 11 | 12 |
| composition obtained in Synthetic Example 1 (based on solid content) | 1.6 | 2.4 | 4.1 | 5.7 | 3.2 | 4.9 | 1.6 | 2.4 | 4.1 | 5.7 | 3.2 | 4.9 |
| composition obtained in Synthetic Example 2 (based on solid content) | 4.9 | 4.9 | 3.2 | 1.6 | 3.2 | 1.6 | 4.9 | 4.9 | 3.2 | 1.6 | 3.2 | 1.6 |

TABLE 1-continued

|  | Example (lauroyl glutamic acid) | | | | | | Example (cocoyl glutamic acid) | | | | | |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| composition obtained in Synthetic Example 3 (based on solid content) | 1.6 | 0.8 | 0.8 | 0.8 | 1.6 | 1.6 | — | — | — | — | — | — |
| composition obtained in Synthetic Example 4 (based on solid content) | — | — | — | — | — | — | 1.6 | 0.8 | 0.8 | 0.8 | 1.6 | 1.6 |
| pH | to pH 9 | to pH 9 | to pH 9 | to pH 9 | to pH 9 | to pH 9 | to pH 9 | to pH 9 | to pH 9 | to pH 9 | to pH 9 | to pH 9 |
| water | to 100 | to 100 | to 100 | to 100 | to 100 | to 100 | to 100 | to 100 | to 100 | to 100 | to 100 | to 100 |
| lather amount after 1 min | 270 | 250 | 245 | 265 | 245 | 265 | 255 | 250 | 255 | 240 | 265 | 240 |
| 5 min/1 min lather retention | 89 | 92 | 92 | 91 | 88 | 87 | 90 | 92 | 88 | 90 | 87 | 90 |
| lather amount | ◎ | ○ | ○ | ◎ | ○ | ◎ | ○ | ○ | ○ | ○ | ◎ | ○ |
| lather retention | ○ | ◎ | ◎ | ◎ | ○ | ○ | ○ | ◎ | ○ | ◎ | ○ | ◎ |
| foamability | ○ | ○ | ○ | ○ | ○ | ○ | ○ | ○ | ○ | ○ | ○ | ○ |
| rinsing | ○ | ○ | ○ | ○ | ○ | ○ | ○ | ○ | ○ | ○ | ○ | ○ |
| after drying | ○ | ○ | ○ | ○ | ○ | ○ | ○ | ○ | ○ | ○ | ○ | ○ |
| weight ratio of lauroylglycine salt/myristoylglycine salt | 0.3 | 0.5 | 1.3 | 3.5 | 1.0 | 3.0 | 0.3 | 0.5 | 1.3 | 3.5 | 1.0 | 3.0 |
| weight ratio of (lauroylglycine salt + myristoylglycine salt)/(lauroyl glutamate or cocoyl glutamate) | 4.0 | 9.0 | 9.0 | 9.0 | 4.0 | 4.0 | 4.0 | 9.0 | 9.0 | 9.0 | 4.0 | 4.0 |

TABLE 2

|  | Comparative Example (lauroyl glutamic acid) | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| composition obtained in Synthetic Example 1 (based on solid content) | 4.1 | 1.6 | 0.8 | 4.1 | — | 2.7 | 1.6 | 3.2 | 1.6 | — |
| composition obtained in Synthetic Example 2 (based on solid content) | 1.6 | 4.1 | 6.5 | — | 4.1 | 2.7 | 3.2 | 1.6 | 1.6 | 7.0 |
| composition obtained in Synthetic Example 3 (based on solid content) | 2.4 | 2.4 | 0.8 | 4.1 | 4.1 | 2.7 | 3.2 | 3.2 | 4.9 | 2.4 |
| composition obtained in Synthetic Example 4 (based on solid content) | — | — | — | — | — | — | — | — | — | — |
| pH | to pH 9 | to pH 9 | to pH 9 | to pH 9 | to pH 9 | to pH 9 | to pH 9 | to pH 9 | to pH 9 | to pH 9 |
| water | to 100 | to 100 | to 100 | to 100 | to 100 | to 100 | to 100 | to 100 | to 100 | to 100 |
| lather amount after 1 min | 240 | 250 | 235 | 230 | 235 | 225 | 240 | 220 | 220 | 250 |
| 5 min/1 min lather retention | 90 | 84 | 89 | 76 | 85 | 91 | 88 | 91 | 84 | 90 |
| lather amount | ○ | ○ | △ | △ | △ | × | ○ | × | × | ○ |
| lather retention | ◎ | △ | ○ | × | ○ | ◎ | ○ | ◎ | △ | ◎ |
| foamability | △ | ○ | ○ | × | △ | △ | △ | × | × | ◎ |
| rinsing | × | △ | ○ | × | × | × | × | × | × | ○ |
| after drying | ○ | ○ | △ | ○ | ○ | ○ | ○ | ○ | ○ | △ |
| weight ratio of lauroylglycine salt/myristoylglycine salt | 2.5 | 0.4 | 0.1 | — | — | 1.0 | 0.5 | 2.0 | 1.0 | — |
| weight ratio of (lauroylglycine salt + myristoylglycine salt)/(lauroyl glutamate or cocoyl glutamate) | 2.3 | 2.3 | 9.0 | — | — | 2.0 | 1.5 | 1.5 | 0.7 | — |

TABLE 3

|  | Comparative Example (cocoyl glutamic acid) | | | | | | | | | | | | |
| --- | --- | --- | --- | --- | --- | --- | --- | --- | --- | --- | --- | --- | --- |
|  | 11 | 12 | 13 | 14 | 15 | 16 | 17 | 18 | 19 | 20 | 21 | 22 | 23 |
| composition obtained in Synthetic Example 1 (based on solid content) | 4.1 | 1.6 | 0.8 | 4.1 | — | 2.7 | 1.6 | 3.2 | 1.6 | 4.1 | 2.4 | 5.7 | — |

TABLE 3-continued

| | Comparative Example (cocoyl glutamic acid) | | | | | | | | | | | | |
|---|---|---|---|---|---|---|---|---|---|---|---|---|
| | 11 | 12 | 13 | 14 | 15 | 16 | 17 | 18 | 19 | 20 | 21 | 22 | 23 |
| composition obtained in Synthetic Example 2 (based on solid content) | 1.6 | 4.1 | 6.5 | — | 4.1 | 2.7 | 3.2 | 1.6 | 1.6 | 4.1 | 5.7 | 2.4 | 5.7 |
| composition obtained in Synthetic Example 3 (based on solid content) | — | — | — | — | — | — | — | — | — | — | — | — | — |
| composition obtained in Synthetic Example 4 (based on solid content) | 2.4 | 2.4 | 0.8 | 4.1 | 4.1 | 2.7 | 3.2 | 3.2 | 4.9 | — | — | — | 2.4 |
| pH | to pH 9 | to pH 9 | to pH 9 | to pH 9 | to pH 9 | to pH 9 | to pH 9 | to pH 9 | to pH 9 | to pH 9 | to pH 9 | to pH 9 | to pH 9 |
| water | to 100 | to 100 | to 100 | to 100 | to 100 | to 100 | to 100 | to 100 | to 100 | to 100 | to 100 | to 100 | to 100 |
| lather amount after 1 min | 235 | 250 | 240 | 215 | 245 | 250 | 240 | 220 | 215 | 265 | 270 | 245 | 260 |
| 5 min/1 min lather retention | 89 | 88 | 88 | 81 | 84 | 88 | 88 | 91 | 88 | 91 | 93 | 86 | 88 |
| lather amount | Δ | ○ | ○ | X | ○ | ○ | ○ | X | X | ◎ | ◎ | ○ | ◎ |
| lather retention | ○ | ○ | ○ | Δ | Δ | ○ | ○ | ◎ | ○ | ◎ | ◎ | ○ | ○ |
| foamability | Δ | ○ | ◎ | X | Δ | Δ | Δ | X | X | ○ | ◎ | ○ | ○ |
| rinsing | X | Δ | ○ | X | X | X | X | X | X | ○ | ○ | ○ | Δ |
| after drying | ○ | ○ | Δ | ○ | ○ | ○ | ○ | ○ | ○ | Δ | Δ | Δ | ○ |
| weight ratio of lauroylglycine salt/myristoylglycine salt | 2.5 | 0.4 | 0.1 | — | — | 1.0 | 0.5 | 2.0 | 1.0 | 1.0 | 0.4 | 2.3 | — |
| weight ratio of (lauroylglycine salt + myristoylglycine salt)/(lauroyl glutamate or cocoyl glutamate) | 2.3 | 2.3 | 9.0 | — | — | 2.0 | 1.5 | 1.5 | 0.7 | — | — | — | — |

TABLE 4

| | Comparative Example (other) | | | |
|---|---|---|---|---|
| | 24 | 25 | 26 | 27 |
| composition obtained in Synthetic Example 1 (based on solid content) | — | — | 8.1 | — |
| composition obtained in Synthetic Example 2 (based on solid content) | — | — | — | 8.1 |
| composition obtained in Synthetic Example 3 (based on solid content) | 8.1 | — | — | — |
| composition obtained in Synthetic Example 4 (based on solid content) | — | 8.1 | — | — |
| pH | to pH 9 | to pH 9 | to pH 9 | to pH 9 |
| water | to 100 | to 100 | to 100 | to 100 |
| lather amount after 1 min | 125 | 160 | 240 | 230 |
| 5 min/1 min lather retention | 64 | 81 | 79 | 91 |
| lather amount | x | x | ○ | Δ |
| lather retention | x | Δ | x | ◎ |
| foamability | x | x | Δ | ○ |
| rinsing | Δ | Δ | ○ | ○ |
| after drying | ○ | ○ | Δ | Δ |
| weight ratio of lauroylglycine salt/myristoylglycine salt | — | — | — | — |
| weight ratio of (lauroylglycine salt + myristoylglycine salt)/(lauroyl glutamate or cocoyl glutamate) | — | — | — | — |

It was confirmed that the cleansing compositions of Examples 1-12 are superior in foamability and lather retention, and further have good sense of use requested for cleansing compositions.

INDUSTRIAL APPLICABILITY

According to the present invention, a cleansing agent superior in foamability and lather retention, and having good sense of use can be provided.

This application is based on patent application Nos. 2016-131878 and 2017-101889 filed in Japan, the contents of which are incorporated in full herein.

The invention claimed is:

1. A cleansing composition, comprising:
   (A) N-lauroylglycine or at least one salt thereof;
   (B) N-myristoylglycine or at least one salt thereof; and
   (C) at least one N-acyl acidic amino acid selected from the group consisting of lauroyl glutamic acid and cocoyl glutamic acid, or a salt thereof,
   wherein a weight ratio of (A)/(B) is 0.3 to 3.5 and a weight ratio of ((A)+(B))/(C) is 4 to 9,
   wherein said composition is a liquid.

2. The cleansing composition according to claim 1, wherein said (C) is lauroyl glutamic acid or a salt thereof.

3. The cleansing composition according to claim 1, wherein said (C) at least one N-acyl acidic amino acid salt is a salt with at least one member selected from the group consisting of sodium, potassium, and triethanolamine.

4. The cleansing composition according to claim 2, wherein said (C) at least one N-acyl acidic amino acid salt is a salt with at least one member selected from the group consisting of sodium, potassium, and triethanolamine.

5. The cleansing composition according to claim 1, wherein said (C) is at least one member selected from the group consisting of N-lauroylglutamic acid, a sodium salt of N-lauroylglutamic acid, a potassium salt of N-lauroylglutamic acid, a triethanolamine salt of N-lauroylglutamic acid, N-cocoylglutamic acid, a sodium salt of N-cocoylglutamic acid, a potassium salt of N-cocoylglutamic acid, and a triethanolamine salt of N-cocoylglutamic acid.

6. The cleansing composition according to claim 1, wherein said (A) N-lauroylglycine salt is a salt with at least one member selected from the group consisting of sodium, potassium, and triethanolamine.

7. The cleansing composition according to claim 2, wherein said (A) N-lauroylglycine salt is a salt with at least one member selected from the group consisting of sodium, potassium, and triethanolamine.

8. The cleansing composition according to claim 3, wherein said (A) N-lauroylglycine salt is a salt with at least one member selected from the group consisting of sodium, potassium, and triethanolamine.

9. The cleansing composition according to claim 4, wherein said (A) N-lauroylglycine salt is a salt with at least one member selected from the group consisting of sodium, potassium, and triethanolamine.

10. The cleansing composition according to claim 5, wherein said (A) N-lauroylglycine salt is a salt with at least one member selected from the group consisting of sodium, potassium, and triethanolamine.

11. The cleansing composition according to claim 1, wherein said (B) N-myristoylglycine salt is a salt with at least one member selected from the group consisting of sodium, potassium, and triethanolamine.

12. The cleansing composition according to claim 2, wherein said (B) N-myristoylglycine salt is a salt with at least one member selected from the group consisting of sodium, potassium, and triethanolamine.

13. The cleansing composition according to claim 3, wherein said (B) N-myristoylglycine salt is a salt with at least one member selected from the group consisting of sodium, potassium, and triethanolamine.

14. The cleansing composition according to claim 4, wherein said (B) N-myristoylglycine salt is a salt with at least one member selected from the group consisting of sodium, potassium, and triethanolamine.

15. The cleansing composition according to claim 5, wherein said (B) N-myristoylglycine salt is a salt with at least one member selected from the group consisting of sodium, potassium, and triethanolamine.

16. The cleansing composition according to claim 1, which has a pH 6 to 10.

17. The cleansing composition according to claim 2, which has a pH 6 to 10.

18. The cleansing composition according to claim 1, wherein said (C) is cocoyl glutamic acid or a salt thereof.

\* \* \* \* \*